US011779491B2

(12) United States Patent
Fu et al.

(10) Patent No.: US 11,779,491 B2
(45) Date of Patent: *Oct. 10, 2023

(54) ADJUSTABLE LASER SURGERY SYSTEM

(71) Applicant: AMO Development, LLC, Irvine, CA (US)

(72) Inventors: Hong Fu, Pleasanton, CA (US); Bryant M. Moore, Pittsboro, NC (US)

(73) Assignee: AMO Development, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/662,397

(22) Filed: May 6, 2022

(65) Prior Publication Data
US 2022/0257415 A1    Aug. 18, 2022

Related U.S. Application Data

(63) Continuation of application No. 16/836,762, filed on Mar. 31, 2020, now Pat. No. 11,324,631, which is a continuation of application No. 14/968,549, filed on Dec. 14, 2015, now Pat. No. 10,610,411.

(60) Provisional application No. 62/115,504, filed on Feb. 12, 2015.

(51) Int. Cl.
  *A61F 9/009*   (2006.01)
  *A61F 9/008*   (2006.01)
  *A61B 18/20*   (2006.01)

(52) U.S. Cl.
  CPC .......... *A61F 9/009* (2013.01); *A61B 18/201* (2013.01); *A61B 18/203* (2013.01); *A61F 9/008* (2013.01); *A61F 9/0084* (2013.01); *A61F 9/00825* (2013.01)

(58) Field of Classification Search
  CPC .... A61F 9/009; A61F 9/00825; A61F 9/0084; A61F 9/008–2009/00897; A61B 18/201; A61B 18/203; A61B 18/20–18/28
  See application file for complete search history.

(56) References Cited

U.S. PATENT DOCUMENTS 5,364,390 A   11/1994  Taboada et al.
5,980,513 A   11/1999  Frey et al.
9,554,857 B2   1/2017  Toledo-Crow et al.
(Continued)

FOREIGN PATENT DOCUMENTS

EP         1486185 A1   12/2004
EP         1731120 A1   12/2006
WO      2008098388 A1    8/2008

*Primary Examiner* — Jonathan T Kuo
(74) *Attorney, Agent, or Firm* — Johnson & Johnson Surgical Vision, Inc.

(57) ABSTRACT

Systems and methods for adjusting an angle of incidence of a laser surgery system include a laser source to produce a laser beam and an optical delivery system to output the laser beam pulses to an object at an adjustable incident angle. A first rotator assembly receives the beam from the laser source along a first beam axis. The first rotator assembly rotates around the first beam axis and the first rotator assembly outputs the beam along a second beam axis different from the first beam axis. A second rotator assembly receives the beam from the first rotator assembly along the second beam axis. The second rotator assembly rotates around the second beam axis. The second rotator assembly follows the rotation of the first rotator assembly and the first rotator assembly is independent of the rotation of the second rotator assembly.

18 Claims, 12 Drawing Sheets

(56) References Cited

U.S. PATENT DOCUMENTS

| | | |
|---|---|---|
| 2003/0208189 A1 | 11/2003 | Payman |
| 2005/0162623 A1 | 7/2005 | Wilson et al. |
| 2010/0094264 A1 | 4/2010 | Rathjen |
| 2010/0211054 A1 | 8/2010 | Lemonis |
| 2013/0338649 A1 | 12/2013 | Hanebuchi et al. |
| 2015/0173835 A1 | 6/2015 | Moeskops et al. |

ADJUSTABLE LASER SURGERY SYSTEM

RELATED APPLICATIONS

This application is a continuation application under 35 U.S.C. § 120 of U.S. patent application Ser. No. 16/836,762, filed Mar. 31, 2020, allowed, which is a continuation application of U.S. patent application Ser. No. 14/968,549, filed Dec. 14, 2015, now U.S. patent Ser. No. 10/610,411, issued Apr. 7, 2020, which is a non-provisional application and claims the benefit under 35 U.S.C. § 119(e) of U.S. Provisional Application Ser. No. 62/115,504, filed Feb. 12, 2015. The above-referenced patent applications are incorporated herein in their entireties by reference.

FIELD OF INVENTION

This disclosure relates generally to a laser surgery system producing a pulsed laser beam for inducing photodisruption at a desired angle to treat a material, such as eye tissue. Although specific reference is made to cutting tissue for surgery, including for example, eye surgery, embodiments as described in this disclosure can be used in many ways to treat many different materials, including for example, cutting optically transparent materials.

BACKGROUND

Vision impairments such as myopia, hyperopia and astigmatism can be corrected using eyeglasses or contact lenses. Alternatively, they can be corrected with eye surgery. Surgeons have traditionally performed eye surgery using manual surgical tools, such as microkeratomes and forceps. More recently, however, laser ophthalmic surgery has gained popularity with lasers being used in a variety of ways to treat visual disorders.

A surgical laser beam is preferred over manual tools because it can be focused accurately on extremely small amounts of ocular tissue, thereby enhancing precision and reliability of the procedure, as well as improving healing time. Indeed, studies show that more patients achieve an improved level of post-operative visual acuity in the months after surgery with a laser system than with manual tools.

Depending on the procedure, and/or the required visual correction or indication, laser eye surgery may involve one or more types of surgical lasers, including for example, ultraviolet excimer lasers, and near-infrared, ultra-short pulsed lasers that emit radiation in the picosecond or femtosecond range. Non-ultraviolet, ultra-short pulsed lasers emit radiation with pulse durations as short as 10 femtoseconds and as long as 3 nanoseconds, and with a wavelength between 300 nm and 3000 nm. Both ultraviolet and non-ultraviolet ultra-short pulsed lasers are used in the commonly-known LASIK (laser in-situ keratomileusis) procedure that is used to correct refractive errors.

With the LASIK procedure, surgeons typically use a non-ultraviolet, ultra-short pulsed laser to cut a superficial flap in the cornea, which is still attached to epithelial tissue in a hinged area. The surgeon lifts the flap to expose the corneal stroma, which he or she then photoablates with an ultraviolet excimer laser to reshape the cornea. Reshaping the cornea helps correct refractive vision problems such as myopia, hyperopia, and astigmatism. Cornea can also be reshaped using other procedures such as photorefractive keratectomy ("PRK").

Besides cutting corneal flaps, ultra-short pulsed lasers are used for other types of eye surgery, including for example, performing incisions for corneal implants, performing intrastromal incisions for refractive correction, as well as for incisions for cataract surgery, such as clear corneal incisions that allow access to the lens capsule, capsulotomy that incises the capsular bag for access to the cataractous lens, and incisions in the lens for softening and segmenting the lens so it can be removed from the eye, and replaced with an artificial intraocular lens.

Conventional ultra-short pulse laser systems have been used to cut tissue and to treat many patients. Many of these systems, however, may provide less than ideal results in at least some instances, particularly, in aligning the eye with the laser surgery system's output beam.

Further, conventional laser surgery systems are physically large, heavy, and stationary and as a result, employ a fixed vertical angle of incidence of the output beam. As illustrated in FIG. 8, a conventional laser beam 800 has a vertical angle of incidence along the Z-axis. The XY plane is parallel to a ground surface while the Z-axis is perpendicular to the ground surface. Some of these conventional laser systems are known to incorporate subsystems that move the output point of the laser beam pulse horizontally and vertically while maintaining the same fixed vertical angle of incidence. While some ultra-short pulse laser systems include a treatment arm or head to output a beam that may be adjusted along the X-axis, Y-axis and Z-axis, other systems include a fixed treatment arm. These systems provide only limited adjustability of the laser beam. Hence, the laser beam's angle of incidence is not adjustable in any current system. Rather, all laser surgery systems provide only a fixed vertical angle of incidence, where the output laser beam is always perpendicular to the plane of the floor.

Because of these limitations, the standard procedure has been to adjust the position of a patient's eye relative to the fixed vertical angle of incidence of the beam. Generally, a patient bed is provided for a patient to lie horizontally such that the patient's eye may be maneuvered to intersect perpendicularly with the laser beam. This fixed angle of incidence, however, may pose constraints on patients with abnormal body shapes and conditions, who are unable to lie flat on a patient bed. Examples of these patients include those with scoliosis or other conditions where the back is abnormally bent, and therefore, cannot lie flat. Indeed, in at least some such instances, the patient's back and head may be tilted such that the beam is unable to intersect the eye perpendicularly even if the eye is aligned directly beneath the beam. In some cases, makeshift solutions, such as pillows, are used to contort the patient's body to temporarily (and at times, precariously) align his or her eye with the laser beam. In severe cases, even makeshift solutions are inadequate, meaning that these patients are unable to receive treatment because they cannot be physically aligned with the vertical laser beam 800, as shown in FIG. 8.

Even for the majority of patients with normal spinal curvatures, subtle misalignment may exist as the eye may not be precisely perpendicular to the laser beam. The eye comprises complex optical structures, and misaligning the eye with the surgical treatment apparatus can result in less than ideal placement of incisions in at least some instances.

For all these reasons, it would be desirable to provide improved methods and systems that overcome at least some of the above limitations of the above prior systems and methods.

SUMMARY

Hence, to obviate one or more problems due to limitations or disadvantages of the related art, this disclosure provides embodiments for improved alignment of a laser beam pulse with an eye during surgery, improved placement of laser beam pulses to incise the eye, improved placement of refractive incisions on the eye, and improved placement of incisions for intraocular lenses. Ideally, these improvements will to provide an improved result for the patient, and provide treatment options to a larger patient population.

Embodiments described in this disclosure provide improved treatment of materials, such as tissue. In many embodiments, the tissue comprises ocular tissue, such as one or more of corneal and lenticular tissue, that are incised for refractive surgery, or one or more of corneal tissues incised during cataract procedures for the placement of intraocular lenses, as well as for treatment of astigmatism. In many embodiments, improved methods and apparatus for performing laser eye surgery are provided for beneficially aligning laser incisions on tissue structures of the eye. Many of the embodiments as disclosed herein are also well suited for combination with laser eye surgery systems that do not rely on patient interfaces, such as laser surgical systems used in combination with pharmacological substances that may affect vision.

The optical structure of the eye may comprise one or more structures of the eye related to optics of the eye, and the tissue structure of the eye may comprise one or more tissues of the eye. The optical structure of the eye may comprise one or more of an optical axis of the eye, a visual axis of the eye, a line of sight of the eye, a pupillary axis of the eye, a fixation axis of the eye, a vertex of the cornea, an anterior nodal point of the eye, a posterior nodal point of the eye, an anterior principal point of the eye, a posterior principal point of the eye, a keratometry axis, a center of curvature of the anterior corneal surface, a center of curvature of the posterior corneal surface, a center of curvature of the anterior lens capsule, a center of curvature of the posterior lens capsule, a center of the pupil, a center of the iris, a center of the entrance pupil, or a center of the exit pupil of the eye. The optical structure of the eye may comprise a pre-contact optical structure determined with measurements obtained prior to the patient interface contacting the eye, or a post-contact optical structure of the eye determined with measurements obtained when the patient interface has contacted the eye.

In a first aspect, a laser surgery system is provided. In many embodiments, a laser surgery system includes a laser source to produce a plurality of laser beam pulses. An optical delivery system is coupled to the laser source to output the laser beam pulses at a predetermined adjustable incident angle. The optical delivery system may include a first rotator assembly receiving the beam from the laser source along a first beam axis. The first rotator assembly may rotate around the first beam axis and the first rotator assembly may output the beam along a second beam axis different from the first beam axis. The optical delivery system may include a second rotator assembly receiving the beam from the first rotator assembly along the second beam axis. The second rotator assembly may rotate around the second beam axis. The second rotator assembly may follow the rotation of the first rotator assembly. Rotation of the first rotator assembly may be independent of the rotation of the second rotator assembly.

In many embodiments, the rotation of the first rotator assembly adjusts one of a polar angle and an azimuthal angle of the beam and rotation of the second rotator assembly adjusts the other of the polar angle and the azimuthal angle of the beam. The first rotator assembly and the second rotator assembly may be beam expanders. In some embodiments, the first rotator assembly and the second rotator assembly may redirect the beam perpendicularly by a respective first mirror and second mirror. The second rotator assembly may output the beam along a third beam axis that is different from the second beam axis.

In some embodiments, a patient interface is coupled to an output of the optical delivery system for docking an eye to the patient interface. The patient interface rotates with the rotation of the first rotator assembly and the second rotator assembly. The first rotator assembly and the second rotator assembly may be axially symmetric. The laser source may be an ultra-short pulsed laser source, such as a picosecond or a femtosecond laser source.

In another aspect, a method of adjusting an angle of incidence of a laser surgery system is provided. In some embodiments, the steps include generating a plurality of laser beam pulses by a laser source. The laser beam pulses are output to an optical delivery system coupled to the laser source. A first rotator assembly may receive the beam from the laser source along a first beam axis. The first rotator assembly may rotate around the first beam axis. The first rotator assembly may output the beam along a second beam axis different from the first beam axis. The second rotator assembly may receive the beam from the first rotator assembly along the second beam axis. The second rotator assembly may rotate around the second beam axis. The second rotator assembly may follow the rotation of the first rotator assembly. The rotation of the first rotator assembly is independent of the rotation of the second rotator assembly. The laser beam pulses may be output by the optical delivery system to an eye at a predetermined adjustable incident angle.

In many embodiments, the rotation of the first rotator assembly adjusts one of a polar angle and an azimuthal angle of the beam and rotation of the second rotator assembly adjusts the other of the polar angle and the azimuthal angle of the beam. The first rotator assembly and the second rotator assembly may be beam expanders. In some embodiments, the first rotator assembly and the second rotator assembly redirect the beam perpendicularly by respective first mirror and second mirror. The second rotator assembly may output the beam along a third beam axis different from the second beam axis.

In some embodiments, a patient interface is coupled to an output of the optical delivery system for docking an eye to the patient interface. The patient interface rotates with the rotation of the first rotator assembly and the second rotator assembly. The first rotator assembly and the second rotator assembly may be axially symmetric. The laser source may be an ultra-short pulsed laser source such as a femtosecond laser source.

In other embodiments, the method further includes the steps of measuring a cornea of an eye, determining an axis of the cornea, determining a rotation of the first rotator assembly and the second rotator assembly to align the incident angle of the output beam with the axis of the cornea, and rotating the first rotator assembly and the second rotator assembly by the determined rotation.

In another aspect, a laser surgery system is provided. In some embodiments, a laser surgery system includes a laser source to produce a plurality of laser beam pulses. A measurement system measures a cornea of an eye. An optical delivery system is coupled to the laser source and the measurement system to output the laser beam pulses at a predetermined adjustable incident angle. The optical delivery system may include a first rotator assembly receiving the beam from the laser source along a first beam axis. The first rotator assembly may rotate around the first beam axis. The first rotator assembly may output the beam along a second beam axis different from the first beam axis. A second rotator assembly may receive the beam from the first rotator assembly along the second beam axis. The second rotator assembly may rotate around the second beam axis. The second rotator assembly may follow the rotation of the first rotator assembly. The rotation of the first rotator assembly is independent of the rotation of the second rotator assembly.

The system may further include a processor coupled to the laser source, measurement system and optical delivery system, the processor comprising a tangible non-volatile computer readable medium comprising instructions to determine an axis of the cornea by the measurement system, determine a rotation of the first rotator assembly and the second rotator assembly to align the incident angle of the output beam with the axis of the cornea, and rotate the first rotator assembly and the second rotator assembly by the determined rotation.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
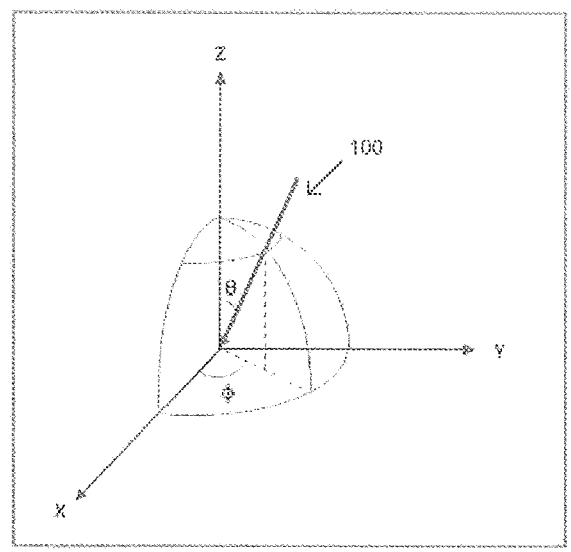
FIG. 1 shows a perspective view illustrating an adjustable angle of incidence of a laser beam according to many embodiments.

The following description describes various embodiments of the present invention. For purposes of explanation, specific configurations and details are set forth so as to provide a thorough understanding of the embodiments. It will also, however, be apparent to one of ordinary skill in the art that embodiments of the present invention can be practiced without certain specific details. Further, to avoid obscuring the embodiment being described, various well-known features may be omitted or simplified in the description.

Methods and systems related to laser eye surgery are disclosed. In many embodiments, a laser is used to form precise incisions in the cornea, in the lens capsule, and/or in the crystalline lens nucleus. Although specific reference is made to tissue cutting for laser eye surgery, embodiments as described herein can be used in one or more of many ways with many surgical procedures and devices, such as microkeratomes and devices used for orthopedic surgery and robotic surgery.

The embodiments as described herein are particularly well suited for treating tissue, such as with the surgical treatment of tissue. In many embodiments, the tissue comprises an optically transmissive tissue, such as tissue of an eye. The embodiments as described herein can be combined in many ways with one or more of many known refractive surgical procedures such as cataract surgery, corneal incisions, LASIK, all laser LASIK, femto LASIK, corneaplasty, astigmatic keratotomy, corneal relaxing incision (hereinafter "CRI"), Limbal Relaxing Incision (hereinafter "LRI"), photorefractive keratectomy (hereinafter "PRK") and Small Incision Lens Extraction (hereinafter "SMILE"), for example. The embodiments as described herein can be particularly well suited for increasing the accuracy of the cutting of the material such as tissue, for example.

The embodiments as described herein are particularly well suited for combination with cataract surgery used for placement of intraocular lenses, as well as for with components of one or more known intraocular lenses such as one or more of accommodating intraocular lenses or intraocular lenses to correct aberrations of the eye. The embodiments disclosed herein can be also used to combine refractive surgical procedures with cataract surgery for placement of intraocular lenses, for example.

The embodiments as described herein can be used to position incisions of the lens capsule sized to receive structures of an intraocular lens in order to retain the placed IOL in alignment with one or more axes the eye as described herein.

The embodiments disclosed herein are well suited for combination with prior laser surgery systems, such as the iFS Advanced Femtosecond Laser, the IntraLase FS Laser, the Catalys Precision Laser System, and similar systems. Such systems can be modified according to the teachings disclosed herein, and to more accurately measure and treat the eye.

As used herein, like characters such as reference numerals and letters describe like elements. As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

The embodiments disclosed herein enable accurate and precise alignment of an eye with an angle of incidence of a beam for subsequent integration with the laser treatment.

Figure 2:
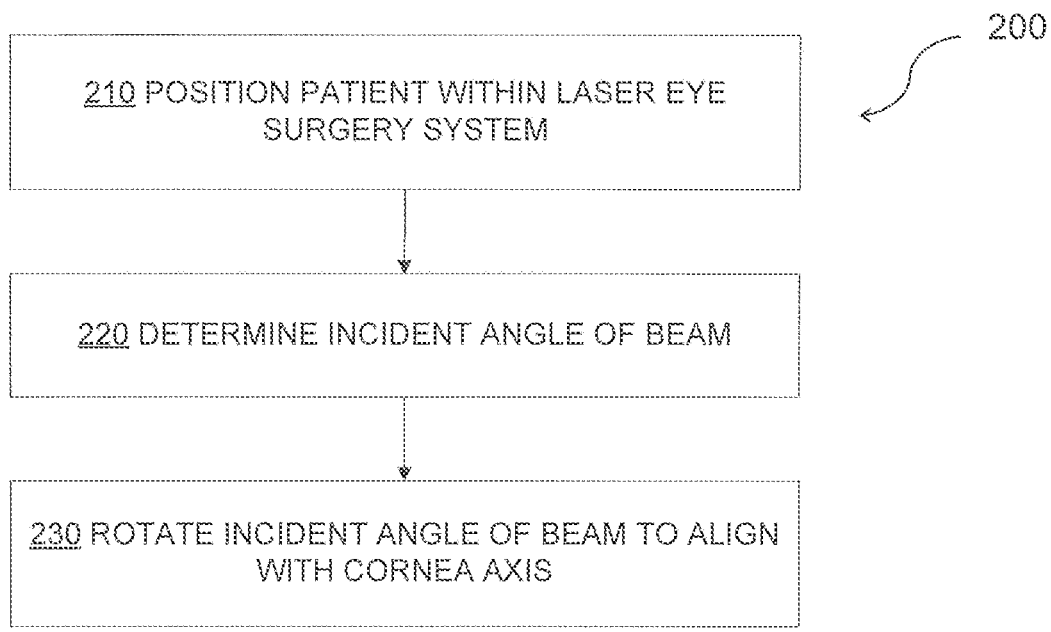
FIG. 2 shows a flowchart of an alignment method of a laser beam with an eye according to many embodiments.

FIG. 1 shows a perspective view illustrating an adjustable angle of incidence of a laser beam, according to many embodiments. An incident angle of beam 100 may be adjusted in a polar angle θ and azimuthal angle φ so as to generate an adjustable beam within a predetermined cone. By introducing two mutually perpendicular rotations about the beam axis in the common propagation path, adjustment of the incident angle is provided within a predetermined range. By providing an adjustable incident angle of the output beam, alignment between the system and eye is improved, leading to improved patient comfort and surgical outcomes. Systems providing an adjustable incident angle, as described in detail below, do not significantly add to the size and weight of a laser surgery system FIG. 2 shows a flow chart of a method 200 for providing alignment of a cornea with an output laser beam, according to embodiments. The method 200 comprises the following main steps. In a step 210, the patient's eye is positioned within the capture/output range of a beam delivery and visualization system 20 of a laser eye surgery system described herein. In a step 220, the visualization system is used to measure the eye and determine a corresponding incident angle of the output beam. Alternatively, an operator such as a surgeon may also visually determine the angle of incidence of the output beam and may input the parameters into a control panel/GUI 50. In a step 230, a rotation mechanism is rotated to output a laser beam that is aligned with the cornea axis determined in step 220.

Figure 3:
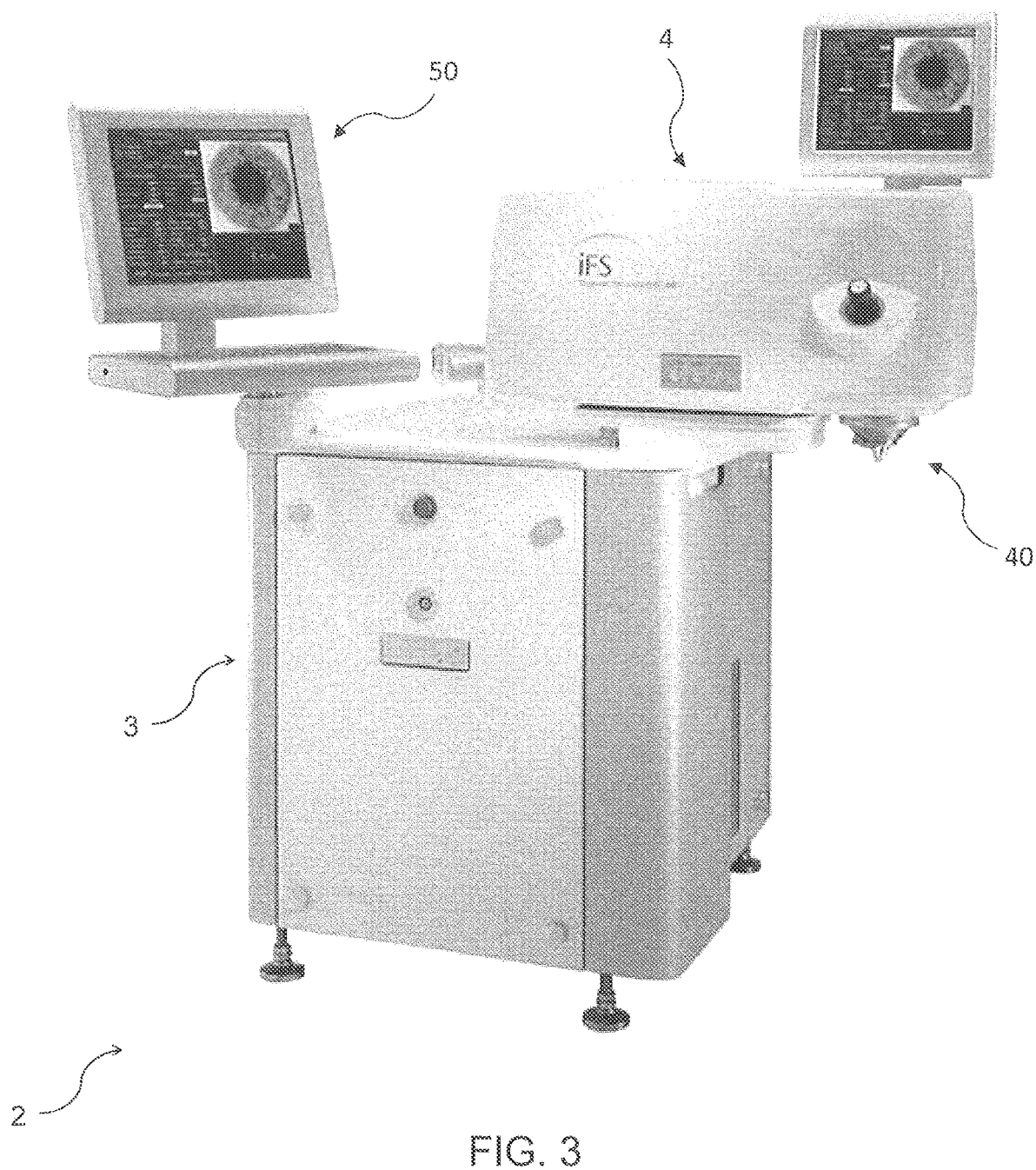
FIG. 3 shows a perspective view showing a laser eye surgery system according to many embodiments.
Figure 4:
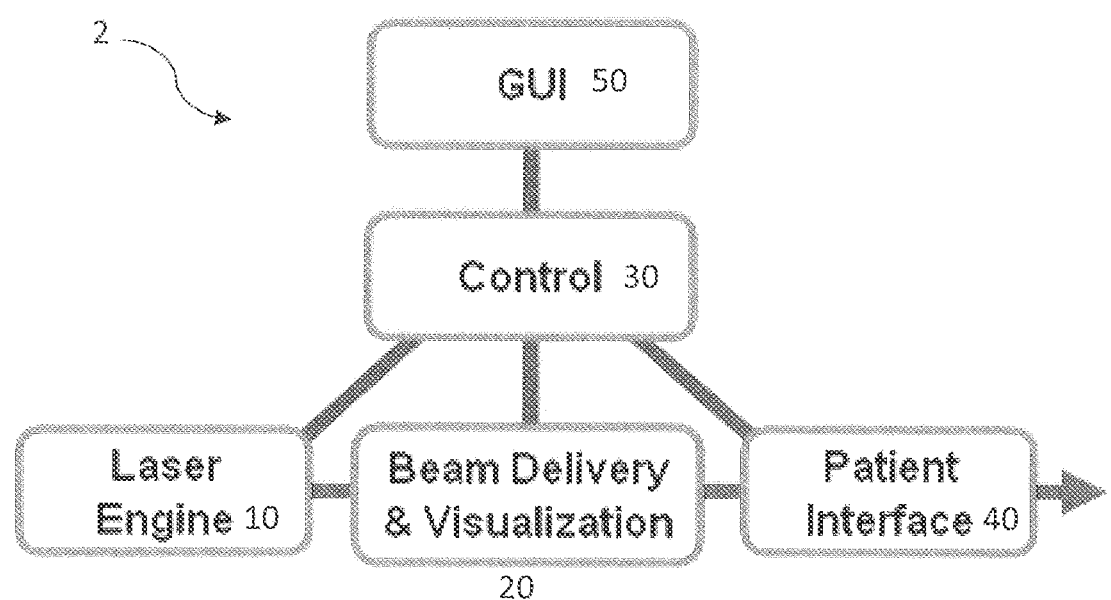
FIG. 4 shows a simplified block diagram showing a top level view of the configuration of a laser eye surgery system according to many embodiments.
Figure 5:
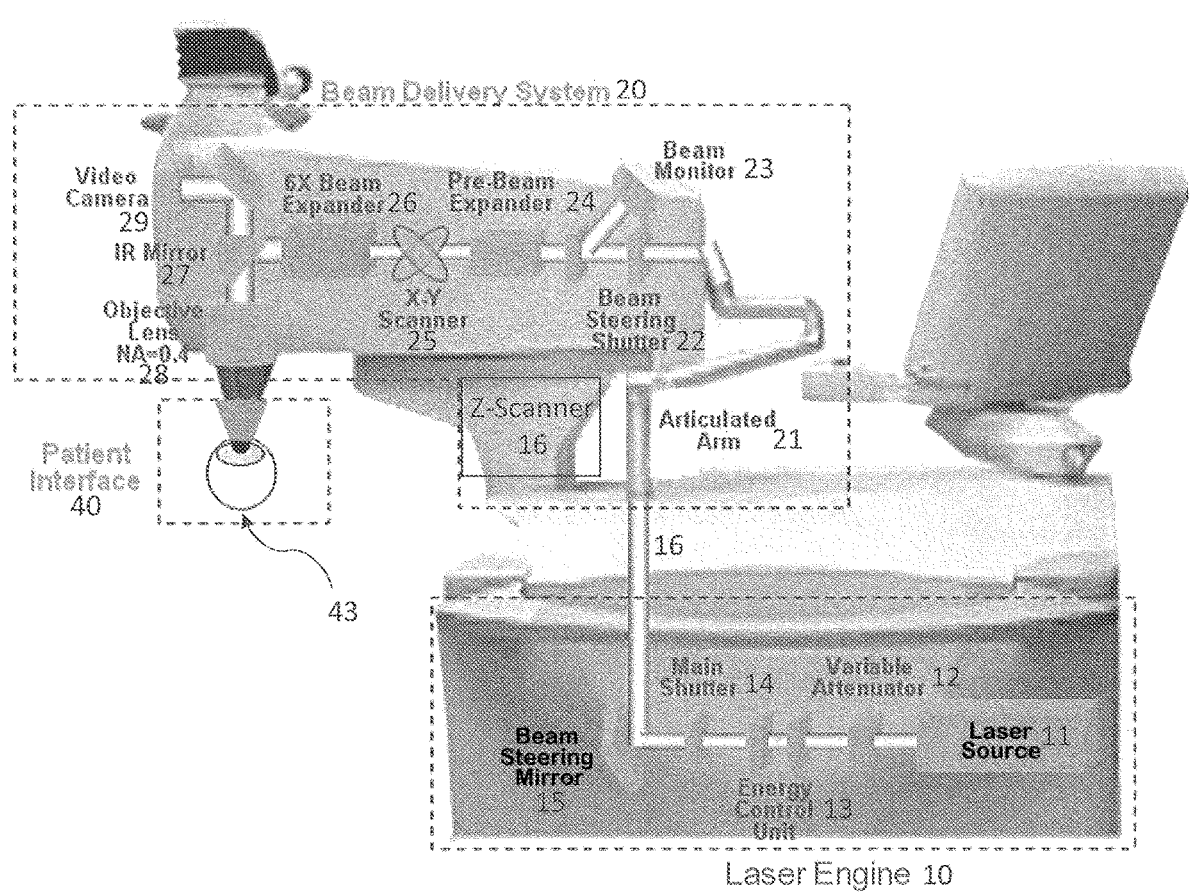
FIG. 5 shows a simplified block diagram illustrating the configuration of a laser eye surgery system according to many embodiments.

Positioning step 210: In the step 210, the patient's eye is positioned within the capture range of a beam delivery and visualization system 20 of the laser eye surgery system 2 as described herein, such as shown in FIGS. 3-5, for example. Positioning of the patient for laser surgery is typically enabled by motion of a patient bed or by motion of the laser system 2. Typically, the operator has manual control of the lateral and axial position, guiding a docking mechanism or patient interface 40 into place. In the absence of a docking mechanism, the operator can be provided with means for guiding the motion so that the eye, such that the cornea is placed within the operative range of the measurement and/or beam delivery system 20. This can be accomplished with the subsystems of iFS and similar systems, with some modifications according to embodiments disclosed herein. Initial patient position can be guided by a video camera 29, guiding the eye into lateral position by centering the video image, and into axial position by focusing the image. At this point, the cornea is placed within the capture range of a measurement system, typically X mm to Y mm axially. For example, an OCT system can be used to measure the axial position of the cornea, and a suitable display 50 provides the operator guidance for final, accurate positioning. Alternatively, a visual imaging system such as a camera, a camera coupled to a microscope which may share optics with the laser system 2, a CCD, among others may be used instead of the OCT system to facilitate the positioning step 210.

For the laser eye surgery system 2, an optical coherence tomography (OCT) system of a beam delivery and visualization system 20 may be used to position the patient eye in the step 210 and/or to measure the shape of the cornea in the step 220. The system 2 may apply any number of modalities to measure the shape of the eye including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack topography of the eye, a Scheimpflug image topography of the eye, a confocal tomography of the eye, or a low coherence reflectometry of the eye. The shape of the cornea can be measured before, during, or after the patient interface 40 is docked with the eye of the patient. Images captured by the beam delivery and visualization system 20 of the laser eye surgery system 2 may be displayed with a display of the control panel/GUI 50 of the laser eye surgery system 2. The control panel/GUI 50 may also be used to modify, distort, or transform any of the displayed images.

Determination step 220: In the step 220, a controller/processor 30 of the laser eye surgery system can be used to determine a degree of rotation of rotation mechanisms(s) to align with the optical axis. An operator may also visually determine the alignment angle. The optical axis of the cornea may be represented as a polar angle and azimuthal angle in a spherical coordinate system where the Z axis is the vertical axis and the XY plane is parallel to ground (FIG. 1). The beam delivery and visualization system 20 can be used to measure one or more optical structures of the eye. The beam delivery and visualization system 20 includes sensors to image one or more tissue structures of the eye and can be used to determine one or more axes of the eye as described herein. The beam delivery and visualization system 20 can image and profile one or more structures of the eye as described herein, such as one or more of the cornea of the eye, the anterior surface of the cornea, the posterior surface of the cornea, the iris of the eye, the pupil of the eye, the natural pupil of the eye, the lens of the eye, the anterior capsule of the lens, the posterior capsule of the lens, the entrance pupil of the eye, the natural entrance pupil of the eye, the vertex of the cornea. In many embodiments, tomography of the cornea is combined with surface topography of the cornea and the video camera images of the cornea to determine one or more axes of the eye. The vertex of the cornea may comprise a central part of the cornea located along the optical axis of the eye that extends substantially perpendicular to the plane of the eye, and may comprise a center of the cornea as determined in response to a measurement of the limbus extending around the perimeter of the cornea.

In many embodiments, a visualization subsystem is used to determine one or more of the optical axis of the eye, the center of curvature of the anterior corneal surface, the center of curvature of the posterior corneal surface, the center of curvature of the lens capsule anterior surface, or the center of curvature of lens capsule posterior surface. The optical axis of the eye may comprise a straight line extending from the center of curvature of the anterior surface of the cornea to the center of curvature of the posterior surface of the posterior lens capsule.

When the corneal surfaces have been mapped, polynomial fitting algorithms or other fitting algorithms can be used to calculate useful parameters of the cornea such as one or more of the axis of the cornea, optical power of the cornea, the astigmatic axis angle, and astigmatism magnitude, for example.

Examples of fitting algorithms suitable for mapping optical tissue surfaces include elliptical surfaces, Fourier transforms, polynomials, a spherical harmonics, Taylor polynomials, a wavelet transform, or Zernike polynomials. In many embodiments, three dimensional elevation profile data of an optical tissue surface of the eye is provided, and the data fit to the optical tissue surface. The optical tissue surface may comprise one or more of the anterior surface of the cornea, the posterior surface of the cornea, the anterior surface of the lens capsule, the posterior surface of the lens capsule, an anterior surface of the lens cortex, a posterior surface of the lens cortex, an anterior surface of the lens nucleus, a posterior surface of the lens nucleus, one or more anterior surfaces of the lens having a substantially constant index of refraction, one or more posterior surfaces of the lens having a substantially constant index of refraction, the retinal surface, the foveal surface, a target tissue surface to correct vision such as a target corneal surface, an anterior surface of an intraocular lens, or a posterior surface of an intraocular lens, for example. As the index of refraction of the lens can vary from about 1.36 to about 1.41, optical surfaces of the lens may define one or more layers of the lens having a similar index of refraction, for example.

Rotation step 230: In the step 230, the incident angle of the output beam is rotated according to the determined rotation of step 220. The rotation mechanism may include a first and second rotator assembly. A rotation of a first rotator assembly and a second rotator assembly may then be determined by the processor to align the incident angle of the output beam with the axis of the cornea.

For example, the processor 30 may instruct the first rotator assembly to rotate by a polar angle θ and the second rotator assembly to rotate by an azimuthal angle φ to rotate the incident angle of the output beam to align with the optical axis. The first rotator assembly and the second rotator assembly are rotated accordingly by two mutually perpendicular rotations each around the axis of the laser beam. Accordingly, the second rotator assembly follows the rotation of the first rotator assembly and rotation of the first rotator assembly is independent of the rotation of the second rotator assembly. By introducing a rotation inside a beam delivery system 20 instead of rotating the system 2 as a whole, the weight of the rotation mechanism is reduced. The processor system may comprise a tangible medium embodying computer program instructions to perform one or more of the method steps as described herein.

FIG. 3 shows a laser eye surgery system 2 according to many embodiments, operable to form precise incisions in the cornea, in the lens capsule, and/or in the crystalline lens nucleus. The system 2 includes a main unit 3 including many primary subsystems of the system 2. For example, externally visible subsystems include a display control panel 50 and a patient interface assembly 4 including patient interface 40. The patient interface assembly 4 is configured to be adjusted and oriented in three axes (X-axis, Y-axis, and Z-axis).

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

FIG. 4 shows a simplified block diagram of the system 2. The system 2 includes a laser engine 10, a beam delivery and visualization system 20, control electronics 30, patient interface 40, and control panel/GUI 50. The control electronics 30 is operatively coupled via communication paths with the laser engine 10, beam delivery and visualization system 20, patient interface 40 and control panel/GUI 50.

The beam delivery and visualization system 20 focuses light to generate a tissue effect, such as photodisruption to treat an eye 43. The beam delivery and visualization system 20 also scans the eye 43 for treatment planning to form a cutting pattern in the eye. In addition, the beam delivery and visualization system 20 provides an output beam with two degrees of freedom to rotate along an azimuthal angle and polar angle in a spherical coordinate system (see FIG. 1).

FIG. 5 shows a simplified block diagram illustrating the configuration of a laser eye surgery system, according to many embodiments. In many embodiments, laser engine 10 incorporates ultra-short pulsed laser, including for example, femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The laser engine 10 can produce laser pulses having a wavelength suitable to the configuration of the system 2. As a non-limiting example, the system 2 can be configured to use a laser engine 10 that produces laser pulses having a wavelength from 1020 nm to 1050 nm. For example, the laser engine 10 can have a diode-pumped solid-state configuration with a 1030 (+/−5) nm center wavelength.

The laser engine 10 can include control and conditioning components. For example, such control components can include components such as a beam attenuator 12 to control the energy of the laser pulse produced by a laser source 11 and the average power of the pulse train, a fixed aperture to control the cross-sectional spatial extent of the beam containing the laser pulses, an energy control unit 13 including one or more power monitors to monitor the flux and repetition rate of the beam train and therefore the energy of the laser pulses, and a shutter 14 to allow/block transmission of the laser pulses. Such conditioning components can include an adjustable zoom assembly to adapt the beam containing the laser pulses to the characteristics of the system 2 and a fixed optical relay 15 to transfer the laser pulses over a distance while accommodating laser pulse beam positional and/or directional variability, thereby providing increased tolerance for component variation.

The beam delivery and visualization system 20 is configured to measure the spatial disposition of eye structures in three dimensions. The measured eye structures can include the anterior and posterior surfaces of the cornea, the anterior and posterior portions of the lens capsule, the iris, and the limbus. In many embodiments, the system 20 utilizes optical coherence tomography (OCT) imaging. As a non-limiting example, the system 2 can be configured to use an OCT imaging system employing wavelengths from 780 nm to 970 nm. For example, system 20 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The beam delivery and visualization system 20 can include a laser or LED light source and a detector to monitor the alignment and stability of the actuators used to position the beam in X, Y, and Z, as well as the polar angle and azimuthal angle of the beam. The system 20 can include a video system that can be used to provide imaging of the patient's eye to facilitate docking of the patient's eye 43 to the patient interface 40. The imaging system provided by the video system can also be used to direct via the GUI 50 the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The generated laser pulse beam 16 proceeds from laser engine 10 through an articulated arm 21. The laser pulse beam 16 may vary from unit to unit, particularly when the laser source 11 may be obtained from different laser manufacturers. For example, the beam diameter of the laser pulse beam 16 may vary from unit to unit (e.g., by +/−20%). The beam may also vary with regard to beam quality, beam divergence, beam spatial circularity, and astigmatism.

After exiting the articulated arm 21, the laser pulse beam 16 proceeds through a beam steering shutter 22. A portion of the beam is reflected to a beam monitor 23. The laser pulse beam 16 proceeds through a pre-beam expander 24 and then a 6× beam expander 26. An IR mirror 27 reflects the emission towards an objective lens 28. The beam is then output through a patient interface 40 to a patient eye 43. A video camera 29 may be provided between the beam expander 26 and objective lens 28.

The beam delivery and visualization system 20 provides a common propagation path that is disposed between the patient interface 40 and the laser engine 10. In many embodiments, the beam delivery and visualization system 20 includes beam expanders 24, 26 to propagate the emission along the common propagation path to the patient interface 40. In many embodiments, the beam delivery and visualization system 20 includes an objective lens assembly 28 that focuses each laser pulse into a focal point. In many embodiments, the beam delivery and visualization system 20 includes scanning mechanisms 17, 25 operable to scan the respective emission in three dimensions. For example, the system 2 can include an XY-scan mechanism(s) 25 and a Z-scan mechanism 17. The XY-scan mechanism(s) 25 can be used to scan the respective emission in two dimensions transverse to the propagation direction of the respective emission. The Z-scan mechanism 17 can be used to vary the depth of the focal point within the eye 43. By themselves, the XY-scan mechanism 25 and Z-scan mechanism 17 do not alter an incident angle of the output beam. In many embodiments, the scanning mechanisms are disposed between the laser diode 11 and the objective lens 28 such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

After reflection by the IR mirror 27, the laser pulse beam 16 passes through an objective lens assembly 28. The objective lens assembly 28 can include one or more lenses. In many embodiments, the objective lens assembly 28 includes multiple lenses. The complexity of the objective lens assembly 28 may be driven by the scan field size, the focused spot size, the degree of telecentricity, the available working distance on both the proximal and distal sides of objective lens assembly 28, as well as the amount of aberration control. After passing through the objective lens assembly 28, the laser pulse beam 66 passes through the patient interface 52.

The beam delivery and visualization system 20 may include a rotation mechanism that allow the pulsed beam output by the system 2 to adjust an incident angle for alignment with the eye, as illustrated in detail in FIG. 6.

The rotation mechanism allowing this angle adjustment are described later in detail, but may be configured along the beam path anywhere between the laser 11 and patient interface 40. Preferably, the rotation components are provided near the patient interface 40 so as to reduce the size and number of subsystems to be rotated. The rotation mechanism may be controlled by the control electronics 30 or by manual adjustment, and can include suitable components, such as a motor, galvanometer, or any other well-known optic moving device. For a rotation mechanism adjacent to the patient interface 40, the rotation mechanism also rotates the downstream patient interface 40. Likewise, if the rotation mechanism is incorporated just after the laser 11 in FIG. 5, then each of the downstream laser engine 10, the beam delivery and visualization system 20 and patient interface 40 are rotated, thus increasing the size and complexity of the rotation mechanism.

The patient interface 40 is used to restrain the position of the patient's eye 43 relative to the system 2. In many embodiments, the patient interface 40 employs a suction ring that is vacuum attached to the patient's eye 43. The suction ring is then coupled with the patient interface 40, for example, using vacuum to secure the suction ring to the patient interface 40. In many embodiments, the patient interface 40 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the beam delivery and visualization system 20 and the patient's eye 43. In many embodiments, the patient interface lens is disposable and can be replaced at any suitable interval, such as before each eye treatment.

The control electronics 30 controls the operation of and can receive input from the laser engine 10, beam delivery and visualization system 20, the patient interface 40, and the control panel/GUI 50 via the communication paths. The communication paths can be implemented in any suitable configuration, including any suitable shared or dedicated communication paths between the control electronics 30 and the respective system components. The control electronics 30 can include any suitable components, such as one or more processor, one or more field-programmable gate array (FPGA), and one or more memory storage devices. In many embodiments, the control electronics 30 controls the control panel/GUI 50 to provide for pre-procedure planning according to user specified treatment parameters as well as to provide user control over the laser eye surgery procedure.

The GUI 50 can include any suitable user input device suitable to provide user input to the control electronics 30. For example, the user interface devices can include devices such as, for example, a control keypad and a patient interface radio frequency identification (RFID) reader. The configuration of FIG. 5 is a non-limiting example of suitable configurations and integration of the laser engine 10, the beam delivery and visualization system 20, and the patient interface 40. Other configurations and integration of subsystems may be possible and may be apparent to a person of skill in the art.

The system 2 is operable to project and scan optical beams into the patient's eye 43. The laser engine 10 includes an ultrafast (UF) laser 11 (e.g., a femtosecond or a picosecond laser). Optical beams can be scanned in the patient's eye 43 in three dimensions: X, Y, Z. For example, short-pulsed laser light generated by the laser 11 can be focused into eye tissue to produce dielectric breakdown to cause photodisruption around the focal point (the focal zone), thereby rupturing the tissue in the vicinity of the photo-induced plasma. In the system 2, the wavelength of the laser light can vary between 800 nm to 1200 nm and the pulse width of the laser light can vary from 10 fs to 100000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43, and specifically within the crystalline lens and the lens capsule of the eye, is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 11 can be a repetitively pulsed 1031 nm device that produces pulses with less than 600 fs duration at a repetition rate of 120 kHz (+/−5%) and individual pulse energy in the 1 to 20 micro joule range.

The laser engine 10 is controlled by the control electronics 30 and the user, via the control panel/GUI 50 to create a laser pulse beam 16. The control panel/GUI 50 is used to set system operating parameters, process user input, display gathered information such as images of ocular structures, and display representations of incisions to be formed in the patient's eye 43.

The XY-scanner 25 is controlled by the control electronics 30, and can include suitable components, such as a motor, galvanometer, or any other well-known optic moving device. The XY-scanner 25 is configured to scan the laser pulse beam 16 in two dimensions transverse to the Z axis and the propagation direction of the laser pulse beam 16. The XY-scanner 25 changes the resulting direction of the laser pulse beam 16, causing lateral displacements of the UF focus point located in the patient's eye 43. Similarly, the Z-scanner 17 is controlled by the control electronics 30, and can include suitable components, such as a motor, galvanometer, or any other well-known optic moving device. The Z-scanner 17 is configured transverse to the XY plane, causing vertical displacements of the UF focus point located in the patient's eye 43.

The beam delivery and visualization system 20 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern need not be identical to the treatment pattern (using the laser pulse beam 16), but can optionally be used to designate the boundaries of the treatment pattern to provide verification that the laser pulse beam 16 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, a ranging beam need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by a video subsystem does not have to be identical to those shared by the treatment beam. The positioning and character of the laser pulse beam 16 and/or the scan pattern the laser pulse beam 16 forms on the eye 43 may be further controlled by use of an input device such as a joystick, or any other appropriate user input device (e.g., control panel/GUI 50) to position the patient and/or the optical system.

The control electronics 30 can be configured to target the targeted structures in the eye 43 and ensure that the laser pulse beam 16 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials places on the docking structures and optical structures of the disposable lens such as the location of the anterior and posterior surfaces.

Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 30 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The system 2 can be set to locate the anterior and posterior surfaces of the lens capsule and cornea and ensure that the UF laser pulse beam 16 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Figure 6A:
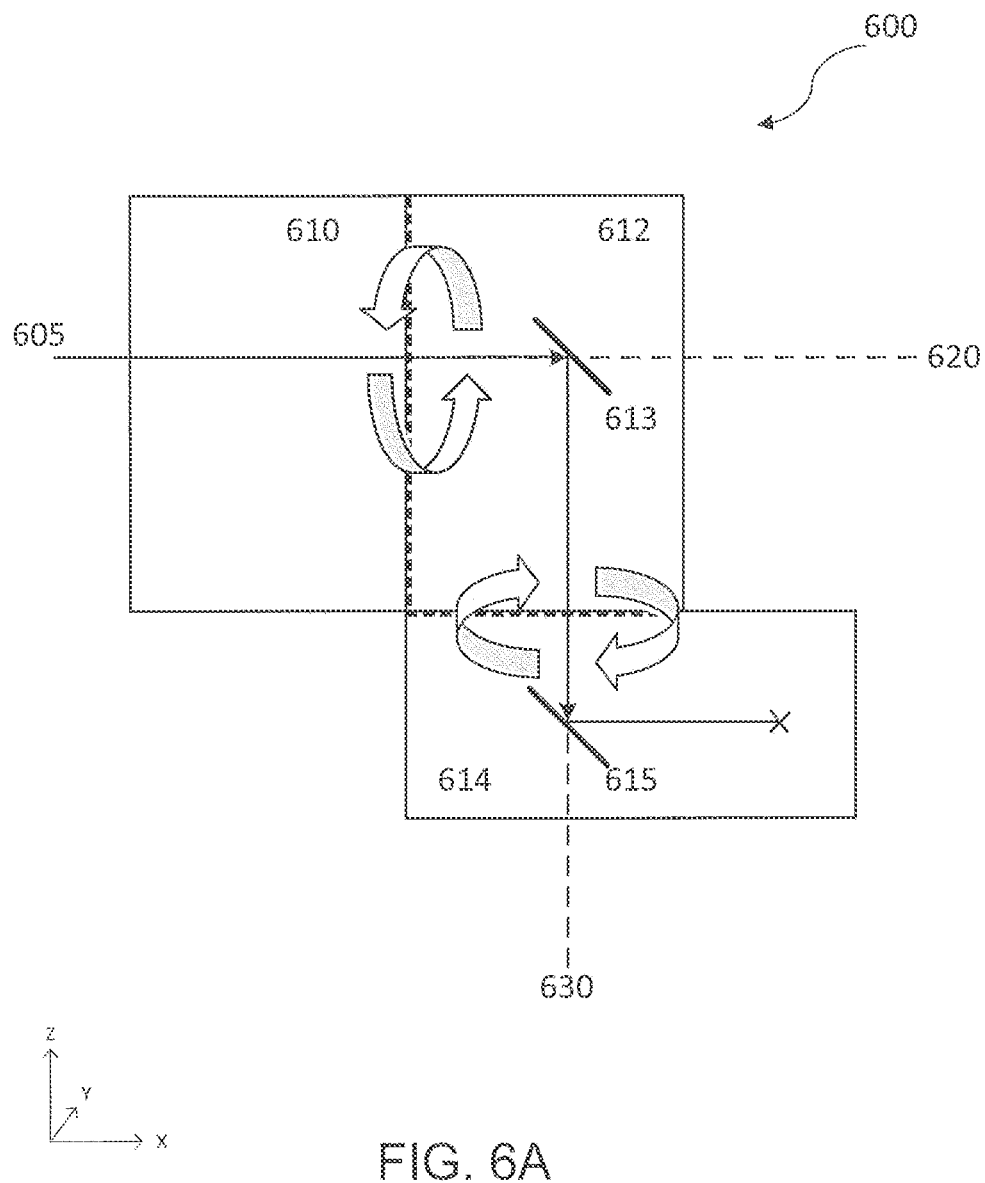
FIG. 6A shows a plan view diagram illustrating the configuration of a beam delivery system of a laser eye surgery system according to many embodiments.

FIG. 6A shows a plan view diagram illustrating the configuration of a beam delivery subsystem 600 of a laser eye surgery system 2, according to many embodiments. The subsystem 600 includes a fixed assembly 610 that does not rotate. The pulsed beam 605 may enter the fixed assembly 610 from a laser engine 10. The beam 605 enters and exits the fixed assembly 610 along a first beam axis 620. The fixed assembly 610 may include a plurality of lenses (not shown), for example.

The beam 605 is then input to a first rotator assembly 612 that rotates relative to the fixed assembly 610 about the first beam axis 620. The first rotator assembly 612 includes a first mirror 613 that preferably reflects the beam 605 perpendicularly from a first beam path to a second beam path. The reflected beam 605 is directed along a second beam axis 630. The beam 605 exits the first rotator assembly 612 along the second beam axis 630. When the first rotator assembly 612 rotates, the first mirror 613 rotates accordingly so as to alter the angle at which the beam 605 is reflected perpendicularly. Due to the rotation of the first rotator assembly 612 about the first beam axis 620, the beam 605 is provided a first degree of freedom for adjustment of the incident angle.

Figure 6B:
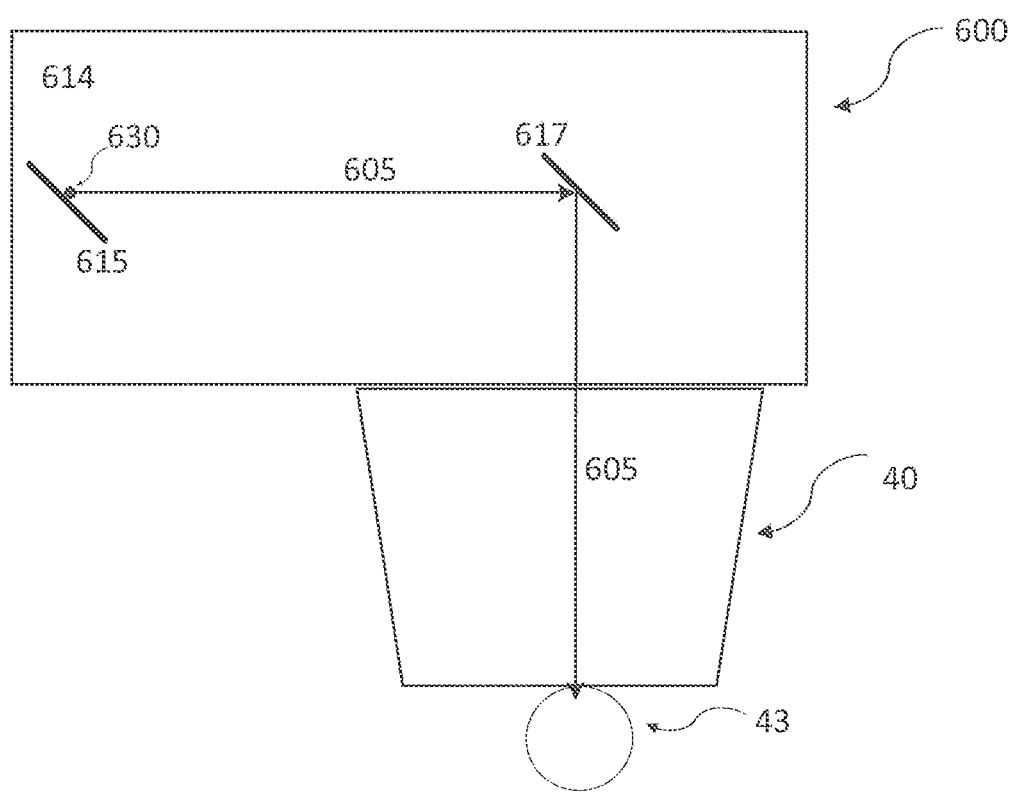
FIG. 6B shows a side view diagram illustrating the configuration of a beam delivery system of a laser eye surgery system according to many embodiments.

The beam 605 is then input to a second rotator assembly 614 that rotates relative to the first rotator assembly 612 about the second beam axis 630. The second rotator assembly 614 includes a mirror 615 that preferably reflects the beam 605 perpendicularly from a second beam axis to a third beam axis. When the second rotator assembly 614 rotates, the second mirror 615 rotates accordingly so as to alter the angle at which the beam 605 is reflected perpendicularly. Due to the rotation of the second rotator assembly 614 about the second beam axis 630, the beam 605 is provided a second degree of freedom for adjustment of the incident angle. The twice-reflected beam 605 is then output to an objective lens assembly 616 (not shown in FIG. 6A). The first rotator assembly 612 and the second rotator assembly 614 may be rotated manually or by controller 30. As best shown in FIG. 6B, the second rotator assembly 614 may include a mirror 617 (not shown in FIG. 6A) that reflects the beam 605 toward a patient interface 40 (not shown in FIG. 6A) for output to an eye 43. The second rotator assembly 614 follows the rotation of the first rotator assembly 612. The rotation of the first rotator assembly 612 is independent of the rotation of the second rotator assembly 614.

Figure 6C:
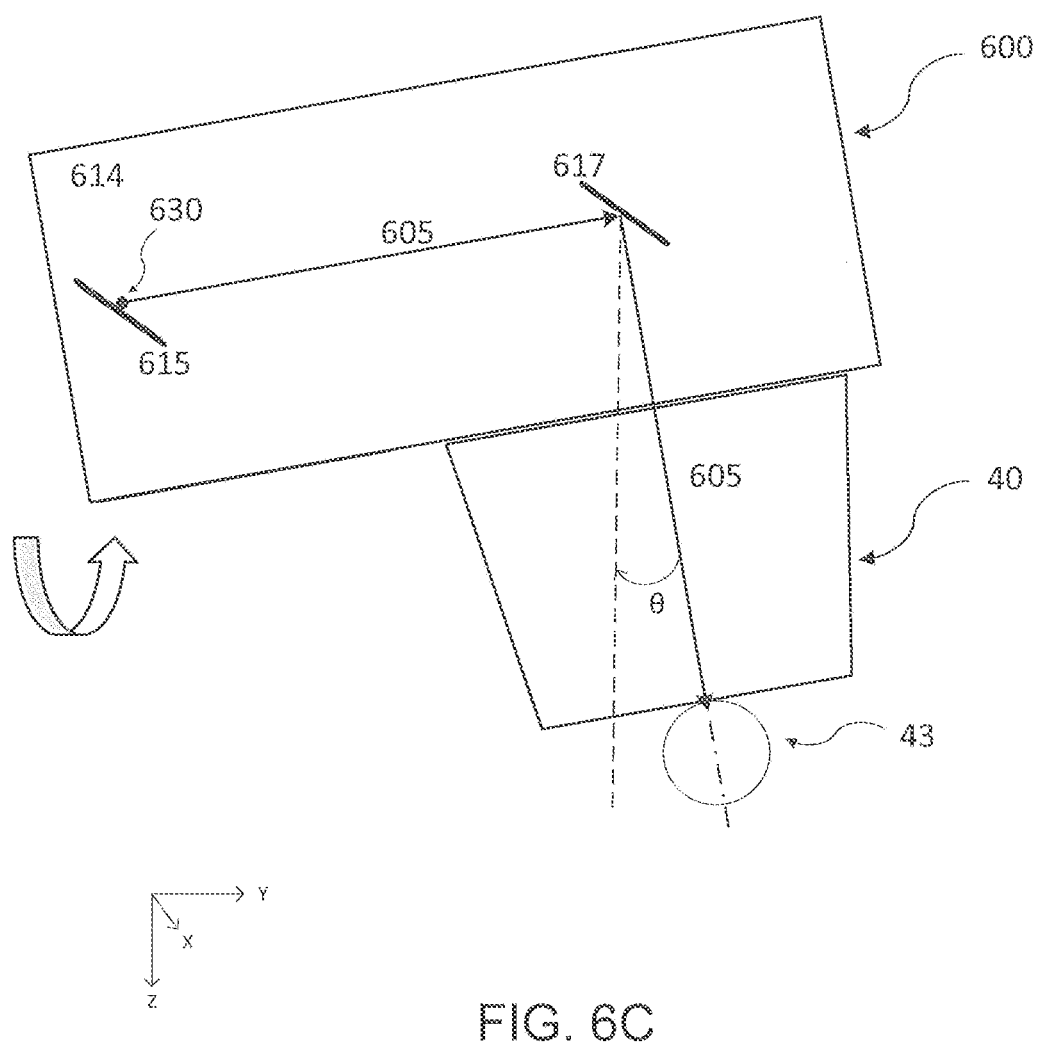
FIG. 6C shows a side view diagram illustrating the configuration of a beam delivery system of a laser eye surgery system according to many embodiments.

FIG. 6B shows a side view diagram illustrating the configuration of a beam delivery system of a laser eye surgery system, according to many embodiments. FIG. 6B illustrates a configuration of the second rotator assembly 614 and patient interface 40 in the YZ plane. FIG. 6B shows a second mirror 615 of the second rotator assembly 614 that reflects the beam 605 along the third beam axis. The second rotator assembly 614 may include a third mirror 617 that redirects the beam 605 perpendicularly towards the patient interface 40. The beam 605 is then output from the patient interface 40 and onto the eye 43. FIG. 6B shows an unrotated subsystem 600 with a vertical incident angle of the beam 605. Although the eye 43 is located directly underneath the beam 605, the eye 43 may be tilted such that optical structures of the eye 43 are misaligned with respect to the vertical beam 605. FIG. 6C illustrates a rotation of the subsystem 600 in the YZ plane for aligning the beam 605 perpendicularly with the optical structures of the eye 43.

FIG. 6C shows a side view diagram illustrating the configuration of a beam delivery system of a laser eye surgery system having the same components of FIG. 6B. The second rotator assembly 614 is rotated about the second rotation axis 630. Rotation of the second rotator assembly 614 rotates the downstream patient interface 40 coupled to the second rotator assembly 614. A second mirror 615 of the second rotator assembly 614 reflects the beam 605 along the third beam axis different from the second beam axis 630. The second rotator assembly 614 may include a mirror 617 that redirects the beam 605 perpendicularly towards the patient interface 40. The beam 605 is then output from the patient interface 40 and onto the eye 43. The incident angle of beam 605 is adjusted by an angle θ to match a tilt of the eye 43 by the rotation of the second rotator assembly 614.

Figure 6D:
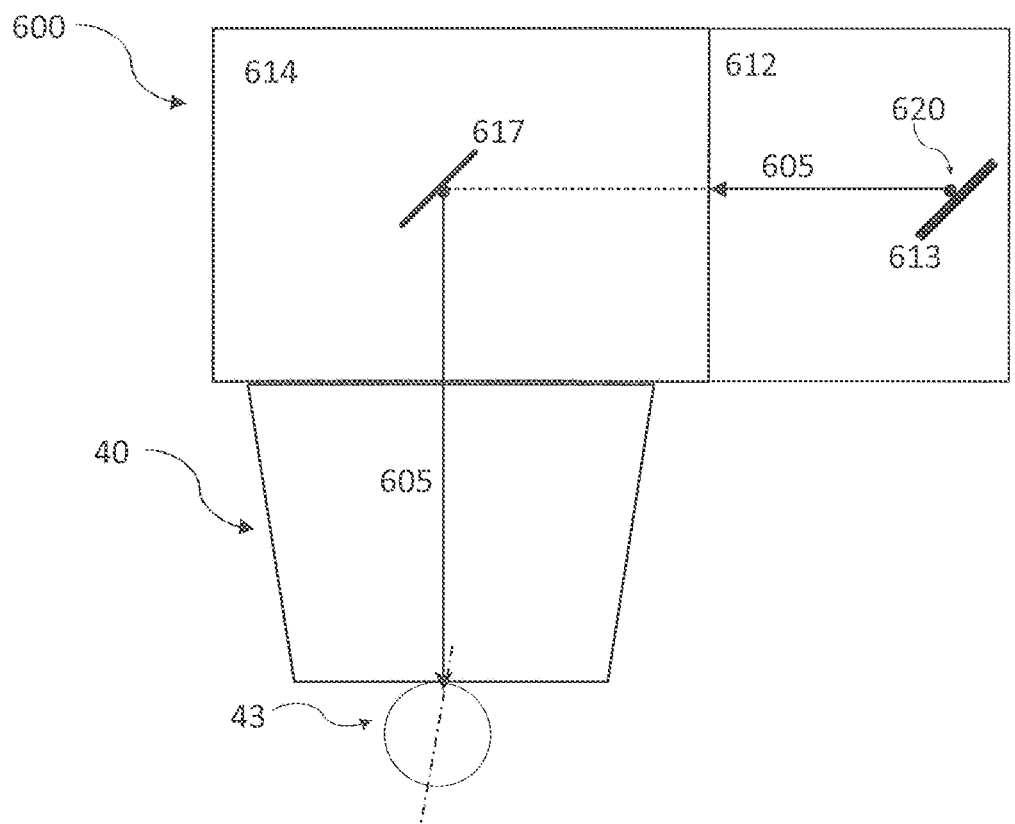
FIG. 6D shows another side view diagram illustrating the configuration of a beam delivery system of a laser eye surgery system according to many embodiments.
Figure 6E:
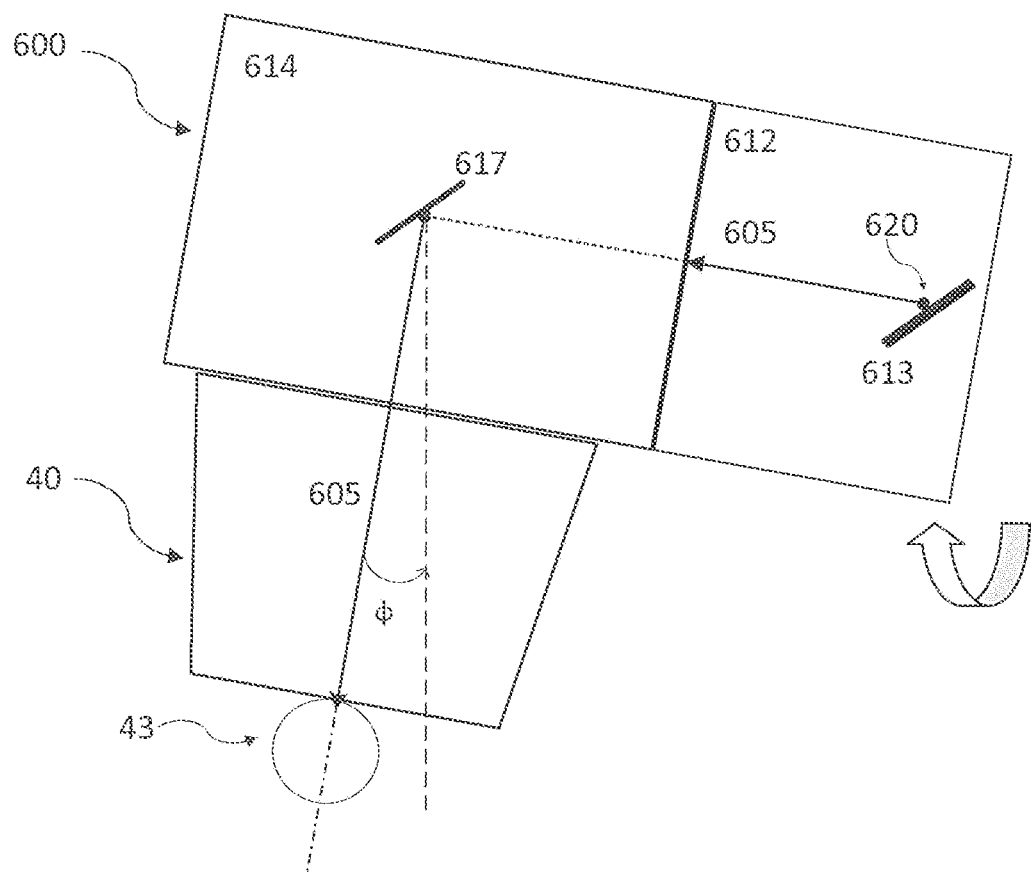
FIG. 6E shows another side view diagram illustrating the configuration of a beam delivery system of a laser eye surgery system according to many embodiments.

FIG. 6D shows another side view diagram illustrating the configuration of a beam delivery system of a laser eye surgery system in the XZ plane including a first rotator assembly 612, second rotator assembly 614 and patient interface 40. The first rotator assembly 612 receives the beam 605 along the first beam axis 620 on a first beam path. The first mirror 613 redirects the beam 605 along the second beam axis 630 on a second beam path towards the second rotator assembly 614. After the second rotator assembly 614 redirects the beam on a third beam path, the mirror 617 redirects the beam 605 perpendicularly downwards towards the patient interface 40. The beam 605 is then output from the patient interface 40 and onto the eye 43. FIG. 6D shows an unrotated subsystem 600 with a vertical incident angle of the beam 605. Although the eye 43 is located directly underneath the beam 605, the eye 43 may be tilted such that optical structures of the eye 43 are misaligned with respect to the vertical beam 605. FIG. 6E illustrates a rotation of the subsystem 600 in the XZ plane for aligning the beam 605 perpendicularly with the optical structures of the eye 43.

FIG. 6E shows another side view diagram illustrating the configuration of a beam delivery system of a laser eye surgery system, according to many embodiments. The first rotator assembly 612 receives the beam 605 along the first beam axis 620 on a first beam path. The first rotator assembly 612 is rotated about the first rotation axis 620. Rotation of the first rotator assembly 612 rotates the downstream second rotator assembly 614 and patient interface 52. First beam mirror 613 redirects the beam 605 along the second beam axis 630 on a second beam path towards the second rotator assembly 614. After the second rotator assembly 614 redirects the beam on a third beam path, the mirror 617 redirects the beam 605 perpendicularly downwards towards the patient interface 40. The beam 605 is then output from the patient interface 40 and onto the eye 43. The incident angle of beam 605 is adjusted by an angle φ to match a tilt of the eye 43 by the rotation of the first rotator assembly 612.

Rotation of first rotator assembly 612 about first axis 620 and rotation of second rotator assembly 614 about second axis 630 provides two degrees of freedom that allow the beam 605 to be adjusted in the polar angle θ and azimuthal angle φ. In this manner, subsystem 600 provides adjustment of an incident angle for patients who are unable to align the optical structures of the eye 43 with a vertical incident angle of a pulsed beam. The output pulse beam is output from the patient interface 40 at any angle within a predetermined cone onto the XY plane. Consequently, the eye 43 need not be strictly perpendicular to the Z-axis.

Figure 7:
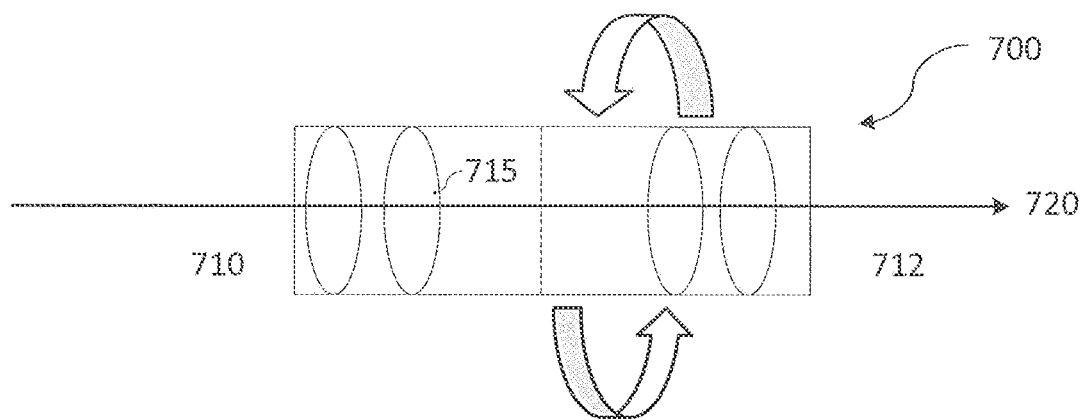
FIG. 7 shows a cross-sectional view of a rotatable beam expander in a beam path of a laser eye surgery system according to many embodiments.
Figure 8:
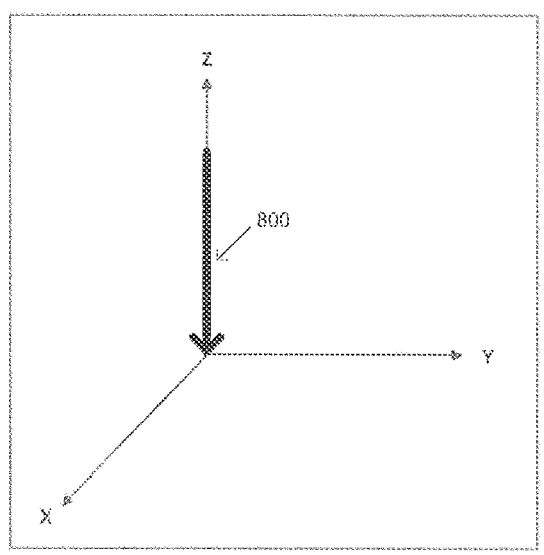
FIG. 8 shows a perspective view illustrating a fixed angle of incidence of a laser beam according to the prior art.

FIG. 7 shows a rotatable beam expander 700 in a beam path of a laser eye surgery system, according to many embodiments. Rotation between the fixed assembly 610 and the first rotator assembly 612, and between the first rotator assembly 612 and the second rotator assembly 614 may be provided by the axially symmetric components illustrated in FIG. 7. For example, a beam expander 700 may include a first section 710 and a second section 712 where the second section 712 is rotated relative to the first section 710 about a beam axis 720. The beam expander 700 may be a tube and may include a plurality of lenses 715, mirrors and other components.

When the second section 712 of the beam expander 700 rotates, the beam itself does not change since the rotation of the expander 700 is about the beam axis 720. However, after redirecting the beam axis perpendicularly by a mirror that rotates with the second section 712, rotation of the second section 712 generates one degree of freedom. Adding a second rotation to the system with another perpendicular redirection of the beam generates a second degree of freedom. If rotation is provided in combination with perpendicular beam redirection, then the polar angle θ is independent of azimuthal angle φ.

However, perpendicularity of the beam redirection is not a requirement so long as the two rotations are non-parallel. For example, mirrors 613 and 615 may redirect the beam 605 at an angle between zero and ninety degrees. In this case, the adjustment of polar angle θ will depend on the degree of rotation of first rotator assembly 612 and second rotator assembly 614, and likewise with azimuthal angle φ. In other words, two non-parallel rotations of the beam also enable adjustment of θ and φ.

In some embodiments, the second section 712 may be L-shaped and include a mirror for redirecting the beam perpendicularly towards another beam expander. The beam delivery subsystem 600 is not limited to rotation of a cutting laser beam for photodisruption. Any of an observation beam, measurement beam and treatment beam generated may be input to a beam expander 700 for adjustment of an incident angle in the same manner as described above.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention. As used herein, the terms first and second are used to describe structures and methods without limitation as to the order of the structures and methods which can be in any order, as will be apparent to a person of ordinary skill in the art based on the teachings provided herein.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A laser surgery system, comprising:
   a laser source to produce a plurality of laser beam pulses;
   an optical delivery system coupled to the laser source to output the laser beam pulses at a predetermined adjustable incident angle, the optical delivery system comprising:
   a first rotator assembly receiving the beam from the laser source along a first beam axis, wherein the first rotator assembly rotates around the first beam axis and the first rotator assembly outputs the beam along a second beam axis different from the first beam axis; and
   a second rotator assembly receiving the beam from the first rotator assembly along the second beam axis, wherein the second rotator assembly rotates around the second beam axis, wherein the second rotator assembly follows the rotation of the first rotator assembly and the rotation of the first rotator assembly is independent of the rotation of the second rotator assembly; and a processor coupled to the laser source and the optical delivery system, the processor comprising a tangible non-volatile computer readable medium comprising instructions to:

receive an input specifying an orientation of the laser beam pulses to be output by the optical delivery system; and control the optical delivery system to rotate the first rotator assembly and the second rotator assembly by respective rotation angles based on the specified orientation.

2. The laser surgery system of claim 1, wherein rotation of the first rotator assembly adjusts one of a polar angle and an azimuthal angle of the beam and rotation of the second rotator assembly adjusts the other of the polar angle and the azimuthal angle of the beam.

3. The laser surgery system of claim 1, wherein each of the first rotator assembly and the second rotator assembly includes a section of a beam expander.

4. The laser surgery system of claim 1, wherein the first rotator assembly and the second rotator assembly redirect the beam perpendicularly by a respective first mirror and second mirror.

5. The laser surgery system of claim 1, wherein the second rotator assembly outputs the beam along a third beam axis different from the second beam axis.

6. The laser surgery system of claim 1, further comprising:

a patient interface coupled to an output of the optical delivery system for docking an eye to the patient interface.

7. The laser surgery system of claim 6, wherein the patient interface rotates with the rotation of the first rotator assembly and the second rotator assembly.

8. The laser surgery system of claim 1, wherein each of the first rotator assembly and the second rotator assembly includes a component that is axially symmetric.

9. The laser surgery system of claim 1, wherein the laser source is a femtosecond laser source.

10. A method for treating an eye using a laser surgery system, the method comprising:

generating a plurality of laser beam pulses by a laser source;

outputting the laser beam pulses to an optical delivery system coupled to the laser source;

by a controller, receiving an input specifying an orientation of the laser beam to be output by the optical delivery system;

directing the beam from the laser source to a first rotator assembly along a first beam axis;

by the controller and based on the specified orientation, controlling the optical delivery system to rotate the first rotator assembly around the first beam axis;

outputting the beam by the first rotator assembly along a second beam axis different from the first beam axis;

receiving the beam by the second rotator assembly from the first rotator assembly along the second beam axis;

by the controller and based on the specified orientation, controlling the optical delivery system to rotate the second rotator assembly around the second beam axis, wherein the second rotator assembly follows the rotation of the first rotator assembly and the rotation of the first rotator assembly is independent of the rotation of the second rotator assembly; and outputting the laser beam pulses by the optical delivery system to the eye to treat the eye.

11. The method of claim 10, wherein rotation of the first rotator assembly adjusts one of a polar angle and an azimuthal angle of the beam and rotation of the second rotator assembly adjusts the other of the polar angle and the azimuthal angle of the beam.

12. The method of claim 10, wherein each of the first rotator assembly and the second rotator assembly includes a section of a beam expander.

13. The method of claim 10, wherein the first rotator assembly and the second rotator assembly redirect the beam perpendicularly by a respective first mirror and second mirror.

14. The method of claim 10, wherein the second rotator assembly outputs the beam along a third beam axis different from the second beam axis.

15. The method of claim 10, further comprising:

coupling a patient interface to an output of the optical delivery system for docking the eye to the patient interface.

16. The method of claim 15, wherein the patient interface rotates with the rotation of the first rotator assembly and the second rotator assembly.

17. The method of claim 10, wherein each of the first rotator assembly and the second rotator assembly includes a component that is axially symmetric.

18. The method of claim 10, wherein the laser source is a femtosecond laser source.

* * * * *